United States Patent [19]

Medeiros et al.

[11] Patent Number: 4,533,743

[45] Date of Patent: Aug. 6, 1985

[54] FURFURAL PROCESS

[75] Inventors: David J. Medeiros, Concord; Mark B. Burnett, Moraga, both of Calif.

[73] Assignee: Atlantic Richfield Company, Los Angeles, Calif.

[21] Appl. No.: 562,123

[22] Filed: Dec. 16, 1983

[51] Int. Cl.³ ............................................. C07D 307/50
[52] U.S. Cl. ..................................................... 549/489
[58] Field of Search ......................................... 549/489

[56] References Cited

U.S. PATENT DOCUMENTS 4,401,514  8/1983  Kanzler et al. ................. 549/489 X Primary Examiner—Richard L. Raymond
Attorney, Agent, or Firm—M. David Folzenlogen

[57] ABSTRACT

Furfural yield and selectivity are maximized by reacting a 1 to 10 percent pentose 0.05 to 0.2 normal mineral acid aqueous solution in a plug flow reactor operated at a temperature between 220° C. and 300° C. The reaction residence time is short and is between 0.5 and 100 seconds. This special high severity plug flow reactor operation may be operated in any configuration to recover the furfural product. Two preferred arrangements are a single phase, pentose recycle operation in which the furfural is recovered by solvent extraction and distillation, and a two phase, solvent recycle operation in which solvent is added to the reactor and furfural is recovered from the solvent by distillation. In some embodiments, the solvent has a boiling point higher than the boiling point of furfural and the ratio of solvent to aqueous phase on a weight to weight basis is between 0.25 and 2.

13 Claims, 2 Drawing Figures

FURFURAL PROCESS

BACKGROUND OF THE INVENTION

This invention is concerned with the production of furfural from pentoses (C-5 sugars) using a continuous plug flow reactor operated under a combination of four special conditions. High furfural yields are obtained with this present invention when the concentration of the reactants are optimized before entry into the reactor and are reacted at unusually high temperatures and short residence times in a plug flow reactor.

Pentosans (C-5 carbohydrates), which when hydrolyzed yield C-5 sugars (pentoses), are the major constituent of biomass hemicellulose. Pentosans can comprise 20–40% of the total dry biomass weight. State-of-the-art biomass acid hydrolysis processing techniques which breakdown pentosans to pentoses can achieve pentose yields to ninety percent of theoretical. Although the pentose hydrolyzate (solution) obtained by such techniques cn be used for other purposes, it can be converted to furfural.

Sources of pentosans include agricultural wastes, such as corn stover, sugar cane bagasse, rice hulls, and corn husks, pulp wastes from paper processing plants, newspaper and wood, and other similar cellulose materials. Pentoses can also be produced as a by-product in conjunction with other chemicals. For example in a wood to ethanol acid hydrolysis process, the wood hemicellulose can first be hydrolyzed to free the pentoses. Further hydrolysis of the remaining cellulose can then be accomplished. Glucose, the sugar derived from cellulose, can then be utilized as feedstock in a number of conversion processes including ethanol fermentation. The use of a by-product pentose stream, such as in the last example, as the feedstock in furfural production help make the overall process economics of this invention more favorable.

Previous inventions have also been concerned with the production of furfural using pentoses and mineral acid catalysts. For example, U.S. Pat. No. 2,536,732 reacts pentose with a mineral acid catalysts in either a continuous or incremental manner in a closed reactor which may be stirred. The reaction temperature is between 100° and 210° C. Reaction times exceed 15 minutes. A suitable furfural solvent is added incrementally or continuously to the reactor in countercurrent fashion. The type of reactor and reactor feed conditions used in U.S. Pat. No. 2,536,732 are not clear, but it is obvious that the reactor is not a plug flow reactor. The aqueous furfural-solvent mixture produced in the reactor is subjected to distillation and the solvent is recycled back to the reactor. U.S. Pat. No. 2,559,607 utilizes 1.5 to 10 percent xylose solution and 1.5 to 5 percent mineral acid catalysts in a tank-type reactor. The reaction temperature and average residence time are 140°–165° C. and 4–10 minutes respectively. The furfural is then extracted with a solvent, for example toluene, in a countercurrent extractor. The remaining aqueous pentose phase can be recycled to the reactor. These two patents use reactors wherein the pentose-acid residence times are distributed about an average lengthy resident time. This requires relatively large volume reactors. If continuous flow reactors of this type are used, reaction advantages based on higher initial concentrations are lost. These and other disadvantages make it difficult to obtain optimum yields and optimum reactor conditions in an efficient manner. The long resident times lead to adverse side reaction conditions. For example, in U.S. Pat. No. 2,559,607 in order to avoid side reactions, the furfural in the conversion zone must be kept below 0.7%. It is the purpose of this invention to provide a combination of four conditions for use with a plug flow reactor whereby the furfural yield is optimized.

Recovery of the product furfural from an aqueous stream can be achieved in a number of manners. Two common approaches being distillation of the furfural rich aqueous phase and solvent extraction of furfural from the aqueous phase with subsequent distillation of the furfural-solvent mixture to obtain the product furfural. U.S. Pat. Nos. 2,536,732 and 2,559,607 illustrate both of these methods. It is another purpose of this invention to provide a plug flow reactor process for producing furfural and recovery techniques to be used in combination with the plug flow reactor.

SUMMARY OF THE INVENTION

In this invention, hot pentose is reacted in the presence of a mineral acid catalyst to maximize furfural yield and selectivity. The process utilizes a plug flow reactor and a combination of four conditions. The concentration of pentose in the pentose-aqueous feed solution before entry into the reactor is between 1 and 10 percent by weight of the aqueous solution before the addition of acid. The concentration of the mineral acid in the reactor is between 0.05 and 0.2 normality before entry into the reactor. The reactor is operated at a temperature between 220° and 300° C. The residence time of the pentose in the reactor is between 0.5 to 100 seconds. This combination of four conditions can be used only in a plug flow reactor to accomplish the objectives of this invention.

A plug flow reactor operated at the aforementioned high severity conditions of high temperatures and short residence times may be used in a number of configurations. Two configurations are preferred. In a first configuration, aqueous unreacted pentose solution separated from the furfural product is combined with fresh pentose feed solution and the reaction occurs in a single-phase, pentose recycle operation. The furfural is recovered by passing the furfural aqueous reactor effluent through a solvent extraction column to separate the aqueous unreacted pentose solution from the furfural-solvent solution. The furfural-solvent phase from the extraction column is subjected to distillation to separate the solvent from the furfural. The separated solvent is then reused in the extraction column. The aqueous phase is recycled to the reactor to utilize unreacted pentose. In a second configuration, solvent is added to the plug flow reactor and the reaction occurs in a two-phase, solvent recycle operation. The aqueous effluent from the reactor is decanted from the furfural-solvent solution by gravity separation. The separated furfural-solvent solution is then subjected to distillation to separate the furfural from the solvent. The solvent is recycled back to the plug flow reactor.

DETAILED DESCRIPTION

Figure 1:
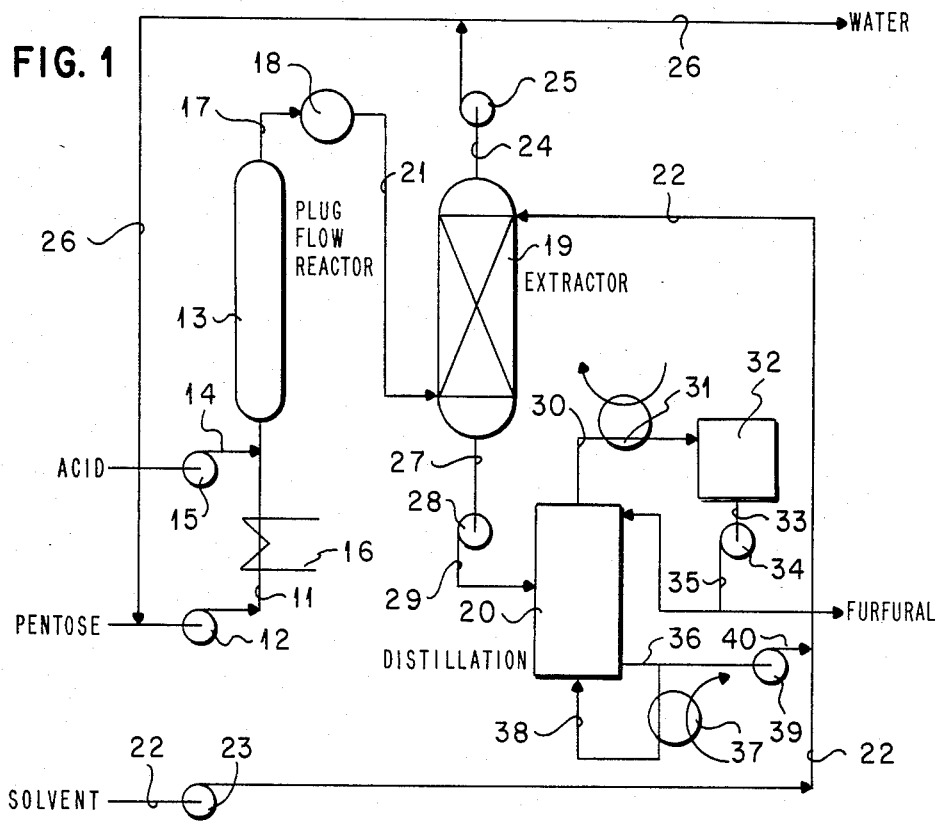
FIG. 1 is a diagrammatic illustration of a single phase, pentose recycle operation in which the furfural is recovered by solvent extraction and distillation.

A hot aqueous solution of pentose in the presence of a mineral acid catalyst reacts to produce furfural. The present invention concerns itself with furfural yield and selectivity improvements over current furfural production technologies. As used in this disclosure, the word "solution" also includes a mixture and a suspension. The words "furfural yield" equal the moles of furfural produced divided by the theoretical potential moles of furfural based on the amount of pentose in feed. The words "furfural selectivity" equal the moles of furfural produced divided by the theoretical potential moles of furfural based on the amount of pentose actually reacted.

Extensive furfural production kinetic studies have been previously reported and kinetic data fitted to proposed mechanisms for the conversion of pentose to furfural using mineral acids catalysts. A reported mechanism is as follows:

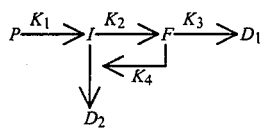

where:
P represents pentose
I a pentose-furfural intermediate
F furfural
$D_1$ and $D_2$ decomposition products
$K_1, K_2, K_3$ first order reaction rate constants
$K_4$ second order reaction rate constants The intermediate I, has not been isolated or identified because once formed it disappears very rapidly (i.e. $K_2 >> K_1$).

Both yield and selectivity are increased at a given reaction time as reaction temperature is increased. In addition, as reaction time is decreased, furfural yield decreases but furfural selectivity approaches 100%. Yield and selectivity also increase with decreased initial pentose concentration. In summary, furfural yield is maximized by maximizing reaction temperature, minimizing initial pentose concentration, and reacting pentose to aproximately 85% of its initial value. Furfural selectivity is maximized by maximizing reaction temperature, minimizing initial pentose concentration and minimizing reaction times. Thus, in this disclosure, maximum furfural yields and selectivity are obtained using low pentose feed concentrations in a plug flow reactor operating at short residence times and high temperature. The high reaction temperatures are between 220° and 300° C. The short reaction times are between 0.5 and 100 seconds. The low pentose feed concentrations are between 1% and 10% by weight of the aqueous solution before the addition of a mineral acid catalyst. The amount of mineral acid catalyst added is sufficient to make the acid normality of the water in the reactor mixture between 0.05 and 0.2.

As previously mentioned, the reaction must be carried out in a plug flow reactor. This type of reactor readily accommodates the above mentioned combination of four reaction conditions thus yielding maximum furfural yields and selectivities. In a plug flow reactor (as distinct from other types of reactors), all fluid elements have essentially the same reactor residence time. Thus, the plug flow reactor can achieve high yields of the furfural products. In a plug flow reactor the concentration of pentose decreases progressively through the reactor whereas in reactors where the fluids are agitated or mixed or flowed countercurrently the concentration of the pentose drops immediately to a low value and portions of the pentose have different resident times. The resident times are distributed about an average resident time, but all of the reactants do not have the same resident time. The plug flow reactors is, therefore, required for the processes of this invention. The plug flow reaction process of this invention is described using two preferred configurations, that is, single phase, pentose recycle reactor/extractor operation, and two phase, solvent recycle operation.

Figure 2:
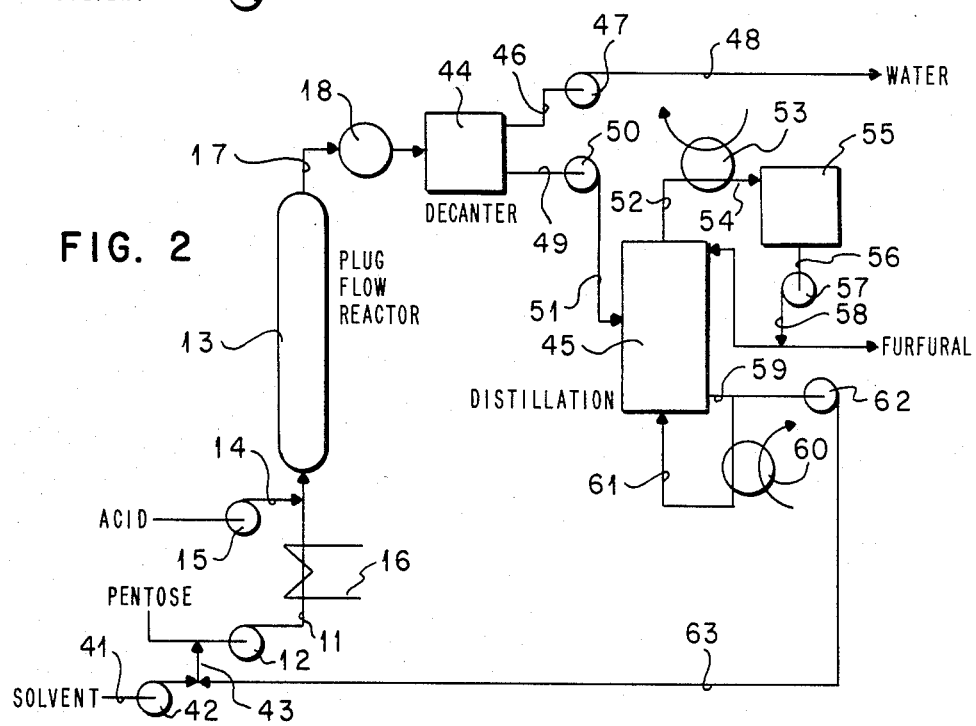
FIG. 2 is a similar illustration of a two phase, solvent recycle operation in which solvent is added to the reactor and furfural is recovered from the solvent by distillation.

In all process configurations, the plug flow reactor is operated at the previously mentioned high severity conditions. Accordingly, as shown in FIGS. 1 and 2, an aqueous pentose (for example xylose) solution containing from 1% to 10% by weight is fed at a suitable pressure through feed line 11 for example by way of pump 12 to plug flow reactor 13. The temperature of the pentose solution can be anywhere from room temperature to the desired pentose to furfural reaction temperature. It is anticipated that the pentose solution will be obtained as a by-product from a wood to ethanol plant (or other biomass wood conversion facilities). In such case, the pentose solution temperature would generally be between 70° and 170° C. Mineral acid (for example, $H_2SO_4$, HCl, etc.) is added to or mixed with the pentose solution in an amount sufficient to make the final reaction mixture have an acid normality of between 0.05 and 0.2. The mineral acid catalyst is fed at a suitable pressure through acid feed line 14, for example by way of pump 15, to plug flow reator 13. The acid may be added to the reactor directly or as shown to the pentose solution before it enters the reactor.

The mineral acid and pentose solutions are fed in a manner such that they mix and pass through the reactor in a plug flow manner. This takes advantage of the high initial concentration of the pentose. The concentration of the pentose decreases as the mixture of solutions flows through the reactor. The reactor is operated in a manner such that the temperature of the reaction is between 220° C. and 300° C. and the residence time of the pentose is between 0.5 and 100 seconds. The length of the reactor (after the mineral acid addition point) can be varied to obtain the desired residence (reaction) time. The reactor will be operated in essentially an isothermal manner. The reactants may be heated in any known manner, such as, steam coils, steam jackets or the like. Preferably, because of the short and controlled residence time, the pentose solution is heated to the necessary temperature by steam jacket heat exchanger 16, or by live steam injection or other suitable heating means, prior to the pentose solution entering reactor 13, and still more preferably, prior to being combined with the mineral acid solution. Preferably, as shown, the mineral acid catalyst (heated or unheated) is added to or combined with the pentose solution before entering the reactor and the heated mixture at the desired reaction temperature between 220° C. and 300° C. is fed into the reactor. The reactor pressure will be above atmospheric pressure and high enough to prevent vaporization of the aqueous solutions. It is anticipated that the reactor pressure will be between 1000 and 2000 psi.

In the reactor the pentose is reacted to furfural and the furfural rich solution is flowed from the reactor through effluent line 17. For example, a reactor was operated in a single phase, single pass manner. The xylose concentration in the feed was 5.0 weight percent. The acid normality of the water in the reaction liquids was 0.1. Sulfuric acid solution was used as the catalyst. The reactor was operated at a temperature of 300° C. and a pressure of 1400 psig. The reaction residence time was between 2 and 3 seconds. The quantity of influent xylose reacted was 90%. The furfural concentration in the aqueous reactor effluent was 2.1 weight percent. From these results, the furfural yield was calculated to be 66% and the furfural selectivity to be 73%. It is expected that furfural yields of 60 to 70% of theoretical can be obtained, the theoretical yield being 64 pounds of furfural per 100 pounds of xylose.

The reactor effluent rich in furfural is decompressed and cooled by expansion valve 18, flashing or other suitable means including, for example, heat exchange. The furfural can then be separated from the reaction products by any of the published methods. For example, the decompressed cooled aqueous furfural solution may be distilled to form a heterogeneous azeotrope of furfural and water containing 35% by weight of furfural which upon being cooled and allowed to settle forms a weaker water-furfural solution which can be recycled to the column and a high concentration furfural solution which is then dehydrated in a second column. But at least two distillation columns are required to produce pure furfural by this method.

The use of two or more distillation columns can be avoided if the furfural is continuously extracted using an essentially water immiscible furfural solvent which does not form an azeotrope with furfural. Therefore, in FIG. 1, the reactor is operated in conjunction with extraction column 19 and distillation column 20. Accordingly, the depressurized, cooled reactor effluent aqueous solution containing furfural is fed by way of extraction inlet line 21 to extraction column 19. The solution could be fed either near the top or at the bottom of the extraction column. In the extraction column, the furfural in the reactor effluent is stripped from the aqueous solution with a suitable solvent. The solvent for the furfural must be immiscible with water, must have an affinity for furfural greater than water has, and must have a density substantially different from that of water. The solvent must be further characterized by the fact that it does not form an azeotrope with furfural. Suitable solvents are higher boiling point aromatics, for example, diethylbenzene, dipropylbenzene, dimenthylethylbenzene, 2-ethyl-2,4-dimenthylbenzene, butylbenzene, tetralin and isophorone; aromatics, such as, toluene; halogenated aromatics, for example, dichlorobenzene, dibromobenzene, bromochlorobenzene and trichlorobenzene; chlorinated diphenyls; halogenated alkanes, for example, 1,1,1-trichloroethane and chloroform; and alkane derivatives, for example, octylalcohol, octylacetate, and ethylacetate. The extraction solvent may be used in cocurrent or countercurrent fashion. As shown, solvent in solvent inlet line 22 via pump 23 is fed into extraction column 19 and flows countercurrently to the reactor effluent liquid injected into the column through line 21. The ratio of the solvent rate divided by the reactor effluent rate fed to extraction column 19 on weight to weight basis is between 0.25 and 2.0. The solvent extracts the furfural to a low concentration; for example, less than 0.05% by weight and an aqueous solution containing unreacted pentose is flowed from the top of the extraction column by way of line 24 and optional pump 25 to recycle/discharge line 26 where it is expected that 75 to 95% of the aqueous solution will be returned to pentose inlet line 11 and recycled through the reactor. Recycle of the unreacted pentose permits using shorter residence times to increase furfural selectivity and achieve higher furfural yield. It also allows lesser amounts of pentose to be reacted per pass than in a single pass reactor. Furfural yields ranging from 80 to 85% of theoretical are possible at reaction times of 0.5 to 5 seconds. For example, a 5% xylose 0.1 normal sulfuric acid solution was reacted at 270° C. and 1,000 psig for 0.5 to 1 second. The quantity of xylose reacted per pass through the reactor was 54%. The amount of xylose solution recycled back to the reactor was 94.5%. The solvent was 1,1,1-trichloroethane and the ratio of solvent to reactor effluent fed to the extraction column was 0.67 on a weight to weight basis. The furfural concentration in the recycled xylose was less than 0.05% by weight. The furfural yield was 82.5% and the furfural selectivity was 90%.

The furfural-rich solvent exits the bottom of the extraction column through line 27 and optional pump 28 where it is fed via line 29 to distillation column 20. The solvent and furfural mixture is distilled in the usual manner. The operation of distillation columns is well known and will not be discussed in detail. The solvent-furfural mixture will be separated with one or the other of the two materials exiting overhead of the column and the other materials exiting through the bottom of the column. This depends upon the relative boiling points between the furfural and solvent. It is much preferred that the solvent have a higher boiling point than the boiling point of furfural. In this manner, the furfural can be recovered as the distillate overhead product of the distillation column. Considerably higher energy requirements would result if the boiling point of the solvent were less than the furfural. Accordingly, as shown, furfural exits the column in overhead line 30 where it would normally be passed through optional cooler or condenser 31 and collected in optional reflux drum 32. Furfural in the reflux drum may be flowed by way of line 33, optional pump 34 and line 35 either back into the distillation column or to storage for the furfural. As shown, solvent is withdrawn from the column in line 36 where some of it, in typical fashion, is heated in heater 37 and recycled through line 38 to the distillation column. Portions of the solvent not recycled are pumped through pump 39 via line 40 into solvent inlet line 222 where the solvent is returned to extraction column 19.

The two-phase, solvent recycle configuration is illustrated in FIG. 2 wherein the plug flow reactor is operated in the manner previously described except that in this embodiment it is unlikely that unreacted pentose will be recycled back to the reactor and in this embodiment furfural solvent is added to the reactor either directly or as shown by way of line 41, optional pump 42 and line 43 to pentose inlet line 11. While in the reactor, furfural is extracted into the solvent phase removing the furfural from the acid catalyst containing aqueous phase. This increases furfural selectivity at the residence times necessary to obtain high furfural yields without the necessity of recycling unreacted pentose. In FIG. 2, the reactor is operated in conjunction with decanter 44 and distillation column 45. Accordingly, depressurized, cooled, reactor effluent aqueous solution containing furfural and solvent is fed into decanter 44 wherein the water and furfural-solvent phases are separated by gravity. In the illustration, the solvent phase has a density greater than the density of the water phase. The water separates overhead to the solvent phase. The water phase is withdrawn through line 46 by way of optional pump 47 and sent through line 48 to disposal or recycle or for any other purpose. The furfural-solvent phase is withdrawn through line 49 and optional pump 50 and fed via line 51 into distillation column 45. If the water phase had a density greater than the furfural-solvent phase the location of lines 46 and 49 would be switched.

The solvent and furfural mixture is distilled in column 45 in the manner previously described. Accordingly, as shown, furfural exits the column in overhead line 52 where it would normally be passed through optional cooler or condenser 53 and line 54 and collected in optional reflux drum 55. Furfural in the reflux drum may be flowed by way of line 56, optional pump 57 and line 58 either back into the distillation column or to the furfural storage. As shown, solvent is withdrawn from the column in line 59 where some of it, in typical fashion, is heated in heater 60 and recycled through line 61 to the distillation column. Portions of the solvent not recycled are pumped through pump 62 into solvent return line 63 where the solvent is returned to reactor 13. The solvent should have the properties previously mentioned. The ratio of the solvent rate divided by the aqueous pentose solution feed rate to reactor 13 will in most cases be between 0.25 and 2.0 on a weight to weight basis. As an example of the results obtained with the configuration of FIG. 2, a 5.5 xylose 0.1 normal sulfuric acid solution was reacted at 280° C. and 1600 psig for 20 seconds. Toluene was used as the solvent despite the fact that its boiling point is less than the boiling point of furfural. The ratio of solvent and aqueous pentose feed was 0.914 on a weight for weight basis. The guantity of xylose reacted was 98%. The furfural yield was 71% and the furfural selectivity was 72%.

Reasonable variations and modifications are possible within the scope of this disclosure without departing from the spirit and scope of this invention.

We claim:

1. A process for the production of furfural from pentosans comprising feeding an aqueous pentose solution containing 1 to 10 weight percent of pentoses into a plug flow reactor, feeding sufficient mineral acid into said plug flow reactor to make the acid normality of the water fed to the reactor to be between 0.05 and 0.2, operating said reactor in a manner such that the temperature of said reactor is between 220° C. and 300° C. and the residence times of said pentose is between 0.5 and 100 seconds and in a manner such that the concentration of pentose decreases progressively through the reactor and all fluid elements of said aqueous solution passing through said reactor have essentially the same residence times, and flowing an aqueous solution containing furfural from said plug flow reactor.

2. The process of claim 1 wherein the aqueous pentose solution is heated prior to entering said plug flow reactor.

3. The process of claim 2 wherein the heated aqueous pentose solution and the mineral acid solution are combined prior to entering said plug flow reactor.

4. The process of claim 1 wherein the furfural is recovered by removing heat from said withdrawn furfural aqueous solution flowed from said plug flow reactor, passing said cooled furfural aqueous solution through an extraction column while passing a solvent for furfural through said extraction column, said solvent being immiscible to water and having an affinity for furfural greater than the affinity of water for furfural, said solvent also having a density different from that of water and being characterized by the fact that does not form an azeotrope with furfural, flowing an extracted aqueous solution from said extraction column and, flowing a furfural solution from said extraction column.

5. The process of claim 4 wherein the amount of solvent fed to said extraction column divided by the amount of aqueous solution passed to said extraction on a weight for weight basis is between 0.25 and 2.

6. The process of claim 4 wherein the solvent has a boiling point higher than the boiling point of furfural.

7. The process of claim 6 wherein the amount of solvent fed to said extraction column divided by the amount of aqueous solution passed to said extraction on a weight for weight basis is between 0.25 and 2.

8. The process of claim 4 wherein at least a part of the aqueous solution withdrawn from said extraction column is recycled to said plug flow reactor as a part of said aqueous pentose solution.

9. The process of claim 1 wherein a furfural solvent is fed to said plug flow reactor, said solvent having a boiling point different from the boiling point of furfural, a density different from water, and an affinity for furfural greater than that of water, said solvent being further characterized by being immiscible with water and not forming an azeotrope with furfural, and a mixture of water and water-immiscible solution of solvent and furfural is flowed from said plug flow reactor.

10. The process of claim 9 wherein heat is removed from said mixture of solvent, water and furfural flowed from said plug flow reactor, the cooled mixture is passed through a decanter to separate water from said immiscible solvent and furfural solution, and said separated immiscible solution is distilled to separate said furfural from said solvent.

11. The process of claim 10 wherein the amount of solvent fed to said plug flow reactor divided by the amount of aqueous pentose solution on a weight for weight basis is between 0.25 and 2.

12. The process of claim 10 wherein the boiling point of said solvent is higher than the boiling point of furfural.

13. The process of claim 12 wherein the amount of solvent fed to said plug flow reactor divided by the amount of aqueous pentose solution on a weight for weight basis is between 0.25 and 2.

* * * * *